(12) United States Patent
Shankaranarayanan et al.

(10) Patent No.: US 7,251,520 B2
(45) Date of Patent: Jul. 31, 2007

(54) METHOD AND APPARATUS OF SLICE SELECTIVE MAGNETIZATION PREPARATION FOR MOVING TABLE MRI

(75) Inventors: Ajit Shankaranarayanan, Mountain View, CA (US); Jean H. Brittain, Palo Alto, CA (US)

(73) Assignee: General Electric Company, Schenectady, NY (US)

( * ) Notice: Subject to any disclaimer, the term of this patent is extended or adjusted under 35 U.S.C. 154(b) by 499 days.

(21) Appl. No.: 10/604,285

(22) Filed: Jul. 8, 2003

(65) Prior Publication Data

US 2005/0020907 A1    Jan. 27, 2005

(51) Int. Cl.
*A61B 5/055* (2006.01)
*G01V 3/00* (2006.01)
*G01V 3/15* (2006.01)

(52) U.S. Cl. .................. 600/415; 600/407; 600/409; 600/410; 600/422; 324/309

(58) Field of Classification Search ................ 600/415, 600/413, 407–410, 422; 324/309, 307; 128/653, 128/922
See application file for complete search history.

(56) References Cited

U.S. PATENT DOCUMENTS

| 5,084,818 | A |   | 1/1992 | Machida |
| 5,111,144 | A | * | 5/1992 | Kuhn .......................... 324/309 |
| 5,327,088 | A | * | 7/1994 | Pipe ............................ 324/309 |
| 5,378,986 | A | * | 1/1995 | Seo et al. .................... 324/309 |
| 5,417,214 | A | * | 5/1995 | Roberts et al. ............. 600/413 |
| 5,423,315 | A |   | 6/1995 | Margosian et al. |
| 5,498,961 | A | * | 3/1996 | Kuhn et al. .................. 324/309 |
| 5,615,677 | A |   | 4/1997 | Pelc et al. |
| 5,636,636 | A | * | 6/1997 | Kuhn et al. .................. 600/415 |
| 5,969,525 | A | * | 10/1999 | Van Driel et al. .......... 324/318 |
| 6,236,738 | B1 |   | 5/2001 | Zhu et al. |
| 6,310,479 | B1 |   | 10/2001 | Zhu et al. |
| 6,385,478 | B1 | * | 5/2002 | Hajnal ........................ 600/410 |
| 6,430,431 | B1 | * | 8/2002 | De Yoe ....................... 600/410 |
| 6,462,545 | B1 | * | 10/2002 | Busse et al. ................. 324/309 |
| 6,509,736 | B2 |   | 1/2003 | Zhu |
| 6,564,080 | B1 | * | 5/2003 | Kimura ....................... 600/410 |
| 6,564,082 | B2 |   | 5/2003 | Zhu |

(Continued)

OTHER PUBLICATIONS

Horvath, L. et al., Total-Body Echo-planar MR Imaging in the Staging of Breast Cancer: Comparison with Conventional Methods—Early Experience, Radiology, 1999, pp. 119-128, vol. 221, No. 1.

(Continued)

*Primary Examiner*—Brian L. Casler
*Assistant Examiner*—Joel Lamprecht
(74) *Attorney, Agent, or Firm*—Ziolkowski Patent Solutions Group, SC

(57) ABSTRACT

The present invention is directed to slice selective magnetization preparation for moving table MRI. The present invention includes a method of magnetization preparation that takes into account patient movement or translation during the imaging process. The present invention adjusts or modifies the frequency at which magnetization preparation pulses are applied to offset the preparation pulse in space. This allows preparation pulses to be interleaved with imaging and enables magnetization preparation without sacrificing other imaging variables or parameters defined for the particular MR study. As such, contrast within a reconstructed image is improved.

19 Claims, 3 Drawing Sheets

U.S. PATENT DOCUMENTS

| | | |
|---|---|---|
| 6,584,337 B2 | 6/2003 | Dumoulin et al. |
| 6,636,756 B2 | 10/2003 | Zhu |
| 6,694,165 B2 | 2/2004 | Zhu |
| 6,721,589 B1 | 4/2004 | Zhu et al. |
| 6,794,869 B2 | 9/2004 | Brittain |
| 6,801,034 B2 | 10/2004 | Brittain et al. |
| 6,879,158 B2 | 4/2005 | Zhu |
| 6,891,374 B2 | 5/2005 | Brittain |
| 6,897,655 B2 | 5/2005 | Brittain et al. |
| 6,915,152 B2 | 7/2005 | Zhu |
| 6,952,096 B2 * | 10/2005 | Freedman .................. 324/303 |
| 7,009,396 B2 | 3/2006 | Zhu et al. |
| 2001/0045830 A1 * | 11/2001 | Maier et al. ................ 324/307 |
| 2002/0115929 A1 | 8/2002 | Machida |
| 2003/0011369 A1 * | 1/2003 | Brittain et al. .............. 324/309 |
| 2003/0100825 A1 | 5/2003 | Demoulin et al. |
| 2003/0180223 A1 * | 9/2003 | McMurry et al. .......... 424/9.36 |
| 2004/0051529 A1 * | 3/2004 | Zhu et al. ................... 324/318 |
| 2004/0113613 A1 * | 6/2004 | Markl et al. ................ 324/306 |
| 2005/0140368 A1 * | 6/2005 | Freedman ................... 324/303 |

OTHER PUBLICATIONS

Johnson, K. et al., Total-Body MR Imaging in as Little as 18 Seconds, Radiology, Jan. 1999, pp. 262-267, vol. 202, No. 1.

Y. Zhu et al., Extended Field-of-View Imaging with Table Translation and Frequency Sweeping, *Magnetic Resonance in Medicine* 49:1106-1112 (2003), Wiley-Liss, Inc.

* cited by examiner

METHOD AND APPARATUS OF SLICE SELECTIVE MAGNETIZATION PREPARATION FOR MOVING TABLE MRI

BACKGROUND OF INVENTION

The present invention relates generally to MR imaging and, more particularly, to a method and apparatus of slice selective magnetization preparation for moving table MRI. More specifically, the present invention relates to the timing and positioning of preparation RF pulses, e.g. inversion recovery pulses, in a pulse sequence for whole body axial imaging of a patient being translated through an imaging volume of an MR system by a moving table.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Moving table MRI is an MR imaging technique that allows for whole body imaging in a relatively short amount of time. Ideally, through continuous translation of a patient through an imaging volume, MR data can be acquired of the chest, abdomen, and pelvis in a single breath-hold. Furthermore, it is preferable for a moving table MR study to provide image quality, contrast, and resolution comparable to stationary or non-moving table studies. Stationary-table studies frequently implement contrast-preparation techniques such as inversion recovery (IR) and saturation recovery to enhance contrast in a reconstructed image. These imaging techniques utilize spatially selective or spatially and spectrally selective RF pulses at a fixed interval in time prior to application of imaging RF pulses and readout gradient pulses. These traditional imaging protocols, however, are not optimal for moving table MRI.

As suggested by its name, moving table MRI uses a table to translate a patient through an imaging volume during the imaging process. The table may incrementally or continuously move the patient through the imaging bore of the MR system. Unlike stationary-table imaging techniques, in moving table MRI, the patient is translated or moved during data acquisition. As such, if a preparatory RF pulse is applied at a moment in time to a particular slice or slab of the patient that is fixed relative to the imaging bore, the tissues subjected to the preparatory pulse will move in the direction of table motion over time. Therefore, a region or volume of interest that was marked for data acquisition may move out of the slice or slab and, as such, not present data for acquisition.

A standard IR pulse sequence 2 for obtaining T1-weighted images of a patient positioned on a stationary stable is illustrated graphically in FIG. 4. As is known, the magnetic moments of the spins in tissue are uniformly aligned upon placement of a patient in a uniform B0 field. This magnetization 3 is then inverted by the application of an RF inversion pulse 4, i.e. 180 degree flip angle, to an imaging volume. Coinciding with the application of the inversion recovery pulse is a slice select gradient 5 that selectively encodes the imaging volume. After the IR pulse 4 is applied, an inversion recovery time TI is observed that allows for the magnetization 3 to recover and decay in accordance with T1 and T2 characteristics of the tissue. The longer TI, the more recovery and decay in the magnetization. At the expiration of TI, another RF pulse 6 as well as slice selective gradient 7 is applied. This RF pulse 6 is generally referenced as an imaging pulse. RF pulse 6 is applied to drive the magnetization of the spins in the tissue back to the transverse plane. Because the RF pulse 6 is preferably applied at TI, those spins that had a zero magnetization are nulled. As illustrated, for T1-weighted imaging, an imaging module 8, i.e. phase encoding and frequency encoding gradients, is applied relatively immediately after RF pulse 6 to acquire MR data from the non-nulled magnetization.

When applied to moving table MRI it is clear that the spins to which the IR pulse was directed, will not only recover toward equilibrium longitudinal magnetization during TI but will move in the direction of table motion. Depending upon the slice/slab thickness set for the particular imaging session and the velocity of table translation, the spins may no longer be in the slice, slab, or volume of interest when TI expires and, as such, not detected during readout.

One possible solution is to adjust the timing of the imaging RF pulse relative to the preparation RF pulse so that the TI period is changed. However, the user selects the appropriate TI period typically as a function of the T1 values of the targeted tissue. Since a preparation RF pulse, such as an inversion RF pulse, causes magnetization to be driven below the transverse plane, the magnetization will progress toward positive magnetization from the inverse or negative magnetization. As such, adjusting TI will not achieve the effect sought with preparation RF pulses and, as such, affects image contrast as well as image intensity; both of which could negatively affect the diagnostic value of the reconstructed image.

Another proposed solution is to acquire imaging data during TI, i.e. as magnetization recovers. However, if data from the imaging volume is collected during the approach from inversion to fully recovered magnetization image contrast will change on a slice-by-slice basis. Variations in image contrast on a per slice basis also negatively affect the diagnostic value of the reconstructed image.

It would therefore be desirable to have a system and method capable of achieving slice selective magnetization preparation for moving table MRI.

SUMMARY OF INVENTION

The present invention provides a system and method of slice selective magnetization preparation for imaging of a patient being translated through an imaging volume by a moving table overcoming the aforementioned drawbacks.

Moving table MRI allows for a whole body exam to be completed in a relatively short period of time. The present invention is directed to slice selective magnetization preparation for moving table MRI. The present invention, which is well suited for gradient echo or spin echo imaging techniques, includes a method of magnetization preparation that takes into account patient movement or translation during the imaging process. In this regard, the present invention adjusts or modifies the frequency at which magnetization preparation pulses are applied without sacrificing other imaging variables or parameters defined for the particular MR study. As such, contrast within a reconstructed image is improved.

Therefore, in accordance with one aspect of the present invention, a method of slice selective magnetization for moving table MRI comprises the steps of defining a fixed imaging slab. The process further includes the step of applying a preparation RF pulse to prepare a region of interest outside the fixed imaging slab. The prepared region of interest is then translated to the fixed imaging slab whereupon an imaging RF pulse is applied to the fixed imaging slab to acquire MR data of the prepared region of interest.

In accordance with another aspect of the invention, an MRI apparatus includes an MRI system having a plurality of gradient coils positioned about a bore of a magnet to impress a polarizing magnetic field and spatially encode spins. An RF transceiver system and an RF switch are controlled by a pulse module to transmit and receive RF signals to and from an RF coil assembly to acquire MR images. The MRI apparatus also includes a computer programmed to receive a user input identifying a preparation interval (e.g. TI) for a pulse sequence to acquire data of a subject being continuously translated through an imaging volume. From the preparation interval, the computer is programmed to determine an offset value, $f_{off}$, to be applied to a preparation RF pulse of the pulse sequence to modify application of the preparation RF pulse to account for translation of the subject through the imaging volume. The computer is also programmed to generate a modified pulse sequence such that application of the preparation RF pulse has been modified by the offset value.

In accordance with another aspect of the invention, the invention is embodied in a computer program stored on a computer readable storage medium and having instructions which, when executed by a computer, cause the computer to determine a distance spins of a prepared tissue of a patient will travel while the patient is translated through an imaging volume by a moving table. The computer is also caused to determine, from the distance, a preparation volume of interest. The instructions also cause the computer to generate an imaging sequence to acquire data from a patient being translated past a fixed imaging volume such that the preparation volume of interest is prepared before being presented in the fixed imaging volume.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

A system is shown to prepare magnetization of a slice, slab, or volume fixed in position relative to a patient being translated continuously through an imaging volume. One skilled in the art will appreciate the present invention is applicable with single slice preparation, multi-slice or slab preparation, or volume preparation. As such, these terms may be used interchangeably throughout the application. The present invention will be described with respect to an inversion recovery, gradient echo pulse sequence; however, the present invention is equivalently applicable with other types of preparation RF pulses, as well as spin echo sequences.

Figure 1:
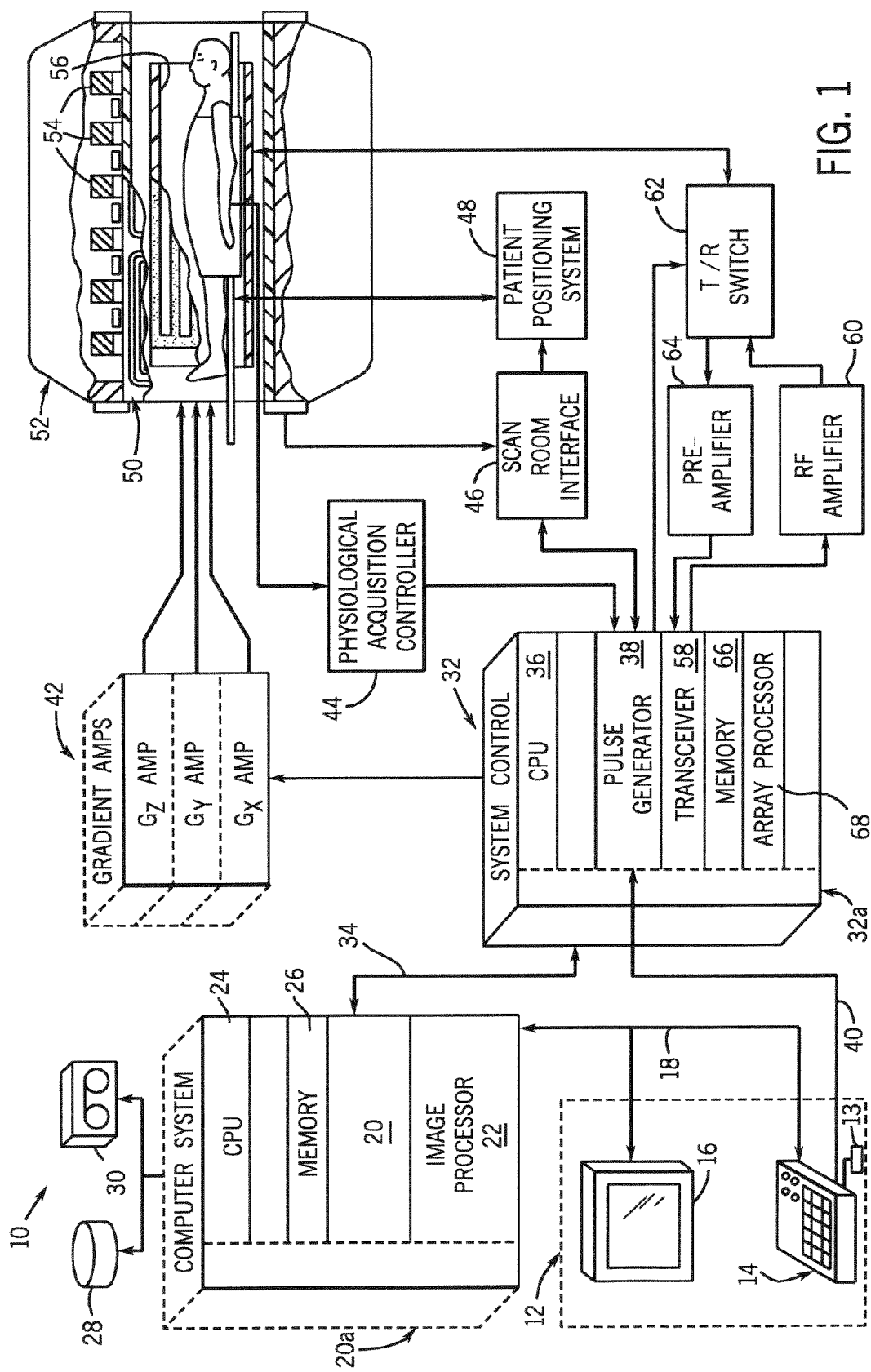
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

The present invention is directed at a method and system of magnetization preparation for moving table MRI. While particularly applicable for whole body axial imaging, the invention is equivalently applicable for other imaging protocols. Additionally, the present invention will be described with respect to continuous translation of the patient, but may be applicable with incremental patient translation. Further, while the present invention will be described for the specific example of an inversion recovery preparation sequence, it is equivalently applicable for other types of magnetization preparation.

It is generally understood that the preparation RF pulses and the imaging excitation RF pulses of a pulse sequence excite the same slice or volume relative to the magnet of the MR system. That is, for moving table MRI, a slice or slab that remains fixed relative to the MR magnet is defined along an imaging axis, i.e. z-axis. As such, as the patient is translated or moved along the imaging axis, different anatomical regions will pass through the slice or slab of interest at different points in time. This allows, for instance, imaging of the pelvis, abdomen, and chest regions of the patient in a single breath-hold. As pointed out previously; however, the tissue or region of interest (or portion thereof) may pass through the fixed slice or slab after a preparation RF pulse is applied but before data acquisition thereby resulting in the region of interest not being completely, if at all, imaged.

Figure 2:
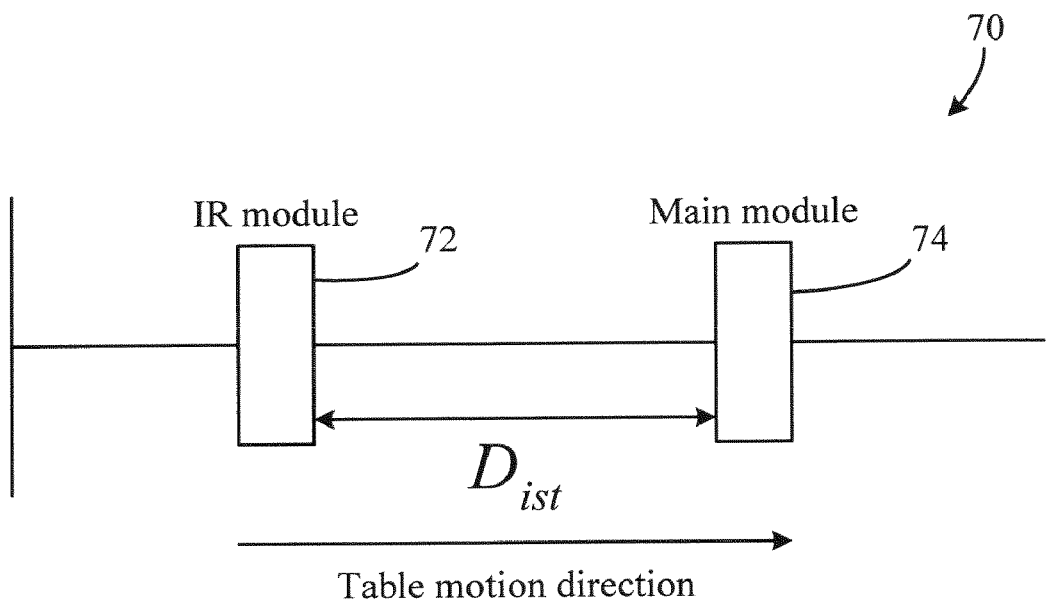
FIG. 2 is a schematic of a portion of a pulse sequence in accordance with the present invention.
Figure 4:
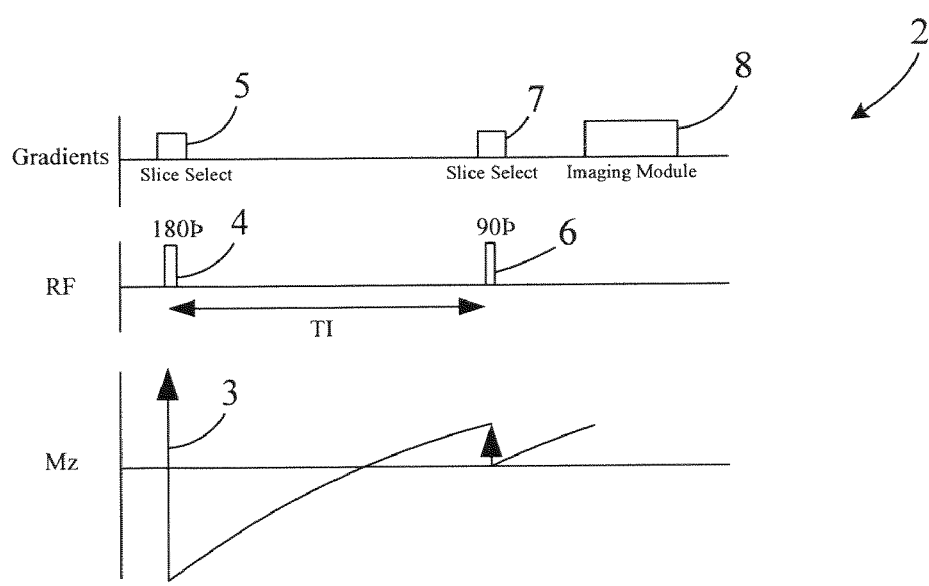
FIG. 4 is a schematic of a known inversion recovery pulse sequence.

Therefore, in accordance with the present invention, and referring to FIG. 2, a diagram showing the spatial relationship of the slices selected by the magnetization preparation and imaging RF pulses 70 for magnetization preparation for moving table MRI is illustrated. Similar to standard imaging sequences, diagram 70 includes an IR or preparation module 72 and a main or imaging module 74. The IR module 72 represents application of a preparation RF pulse, i.e., an inversion recovery pulse having a flip angle of 180 degrees, as well as spoiler gradients to dephase any magnetization inadvertently tipped into the transverse plane. The preparation RF pulse may be a spatially selective, or a spatially and spectrally selective RF pulse. Module 74 represents the imaging RF pulse as well as the encoding and readout gradients that follow. It should be noted that the present invention is applicable with gradient as well as spin echo imaging techniques including rapid imaging variations such as echo-planar imaging, spiral imaging, projection reconstruction, and fast spin echo.

As shown in FIG. 2, the IR module 72 occurs before imaging module 74 in both space and time. That is, as the table moves the patient along a translation direction, the pulses of the IR module are first applied to invert a volume of interest different from an imaging volume (both with respect to the MR magnet) and are followed by application of the pulses of the imaging module at some predefined period of time, TI, thereafter. Since the patient is being moved parallel to table motion direction, the spins in the tissue of the patient will be prepared, i.e. inverted, at a point in time and space before those spins reach the imaging volume. As will be described below, the spins will be subjected to the preparation RF pulse at a moment that is a function of recovery time, TI. The velocity by which the table moves the patient passed the fixed slice or slab and the recovery time, TI, determine the distance separating the preparation volume from the imaging volume.

As will be described in greater detail below, the IR module is applied to a set of spins of a tissue that is not in the imaging volume fixed relative to the MR magnet when the IR pulse is applied. That is, the IR module is applied to an inverted volume different from the imaging volume. Since the patient is being continuously translated through the bore of the MR magnet, MR data may be acquired of the imaging volume while the spins of the inverted volume recover. As such, the spins of the imaging volume may be prepared prior to reaching the imaging volume that remains fixed relative to the MR magnet. This allows for nearly continuous data acquisition of the patient as it translates through the imaging volume while simultaneously allowing for preparation of a soon-to-be imaged tissue or inverted volume, i.e. prior to the soon-to-be imaged tissue entering the imaging volume. The preparation sequence can be temporally interleaved with the imaging sequence. In this regard, data acquisition of the imaging volume is minimally affected by the inversion recovery time, TI.

In continuously moving table MRI, the distance, $D_{ist}$, a particular spin will travel within a single recovery time, TI, can be determined based on table or patient velocity, v, and the value set for TI by the user when prescribing the scan study. That is, the distance traveled by a spin following application of an IR pulse is:

$$D_{ist} = v \cdot TI \qquad \text{(Eqn. 1).}$$

From the product of the recovery time and the velocity of table motion, a pulse frequency offset value, $f_{off}$, can be determined in accordance with the following:

$$f_{off} = \gamma \cdot A_{ss} \cdot D_{ist} \qquad \text{(Eqn. 2),}$$

where $\gamma$ represents the gyromagnetic ratio of 42.58E6 Hz/T and $A_{ss}$ represents the amplitude of the slice selective gradient applied during the preparation RF pulse. The pulse frequency offset value is applied to the standard frequency of the preparation RF pulse to be applied in the absence of table movement. For example, if the operator selects a TI of 100 ms and the table velocity of 1.25 cm/sec then the $D_{ist}$ would be 12.5 mm leading to a particular frequency offset value for the IR preparation RF pulse. The application of the inversion pulse would be TI time earlier than the acquisition of the corresponding data set. It should be noted that the inversion pulse sequence is interleaved with the imaging pulse sequence and as the acquisition of the appropriate data set starts the prepared volume enters the imaging volume courtesy of the table movement. Since the offset is to be applied in a direction that is opposite of table motion, this allows the inverted volume to recover in time as it moves in space to the imaging volume defined by the fixed slice or slab relative to the MR magnet. The TI period remains the same. It should be noted that the size of the optimal volume of the MR scanner limits the maximum distance between the volumes selected by the preparation pulse and the imaging pulse. Therefore, $D_{ist}$ should be smaller than the size of the optimal imaging volume in the direction of table motion. It should also be noted that since the preparation RF pulse is interleaved with the imaging pulse, there is nearly continuous acquisition of data leading to efficient collection of the data while achieving the desired contrast.

Applying the preparation RF pulse at the offset frequency value allows for the spins that are the subject of data acquisition to not only recover from the inverted magnetization during TI, but also allows for the spins to be translated during that same TI period in space such that the prepared magnetization are presented at the time period for data acquisition. In this regard, in one embodiment, the preparation RF pulses may be applied or played out with the same slice thickness as the imaging RF pulses and are repeated at an interval that coincides with the amount of time necessary for the table to translate the patient one slice thickness.

However, one skilled in the art will appreciate that the repetition interval of the preparation pulses, i.e., time between application of preparation RF pulses, could be set to a value different from that needed for the table to move the patient one slice thickness. Further, the slice thicknesses of the preparation pulse and the imaging RF pulses may be different and this could impact the repetition interval. Additionally, the repetition interval of the preparation pulse can be changed as desired for a particular MR study. To further enhance contrast differences as well as the robustness of the moving table MRI, the type of preparation pulse could be varied as the table is moved to achieve different contrast properties or different image quality. In yet a further embodiment, the offset could be varied, depending on the goals of a particular study, on a per TR basis. As such, different parts of the anatomy could be imaged differently. In this regard, the present invention not only improves the contrast and effectiveness of moving table MRI, it improves the flexibility and quality of image contrast.

Figure 3:
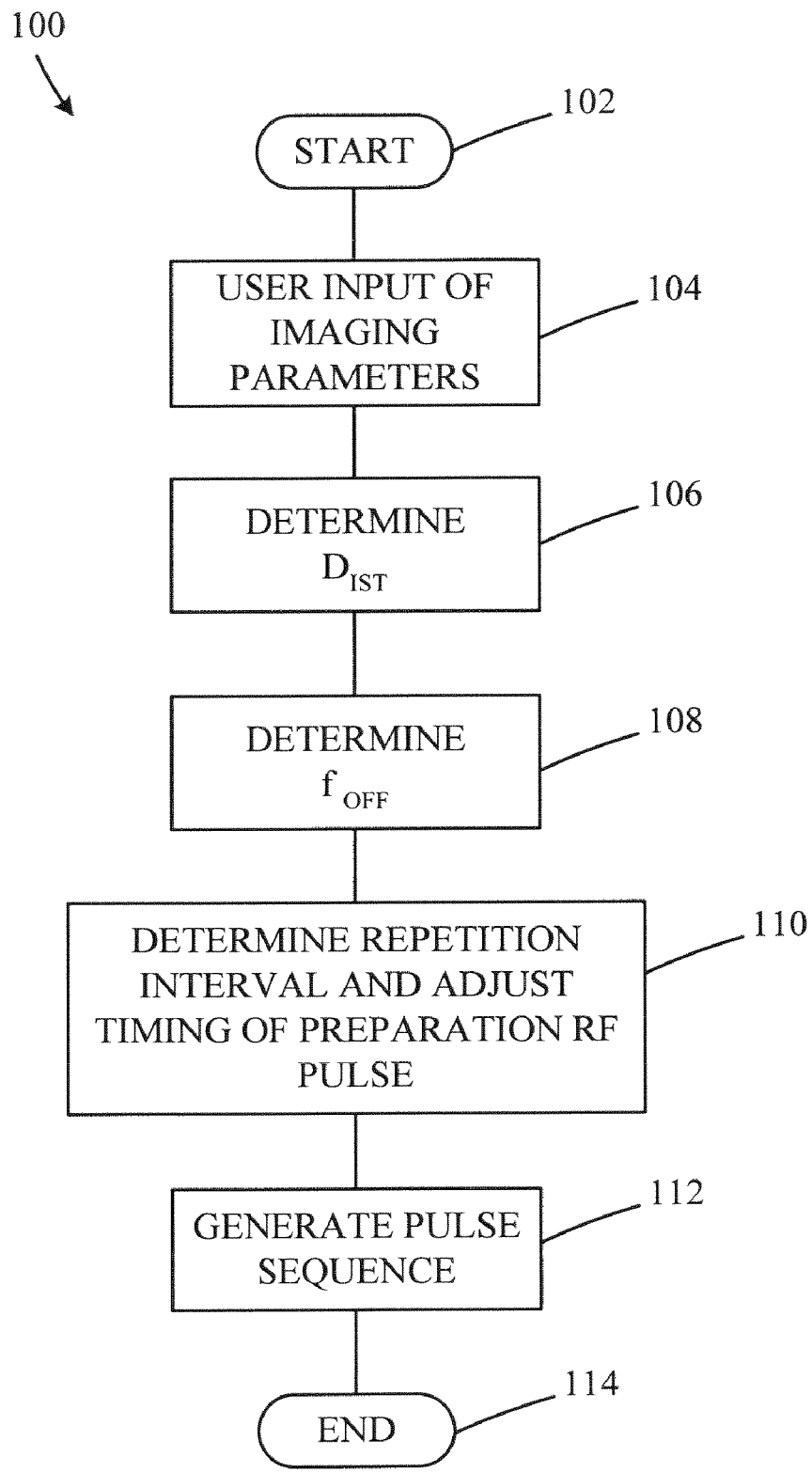
FIG. 3 is a flow chart setting forth an imaging pulse in accordance with the present invention.

Referring now to FIG. 3, the steps of an imaging process implementing the present invention is shown. The process 100 begins at 102 with a patient being positioned on a table for MR imaging. Shortly thereafter, an MR technologist or radiologist inputs at step 104 a series of imaging parameter identifiers that could include TR, T1 and T2 values of a targeted tissue, type of imaging sequence, type of preparatory pulses to be applied, TI, flip angles, table velocity, slice thickness, k-space dimensions, and the like. From the table velocity and TI values entered (or analogous parameter for a different type of contrast preparation), the distance a spin will travel during the TI at the identified table velocity is determined at step 106 in accordance with Equation 1. From the distance determined by Equation 1, the frequency offset to apply in accordance with Equation 2 is determined at 108. The repetition interval and timing of the preparation pulse is the determined at 110. In accordance with the user inputs at step 104, the offset of the magnetization preparation pulse at 108, and the timing and repetition interval of the preparation RF pulses at step 110, a pulse sequence tailored to the imaging parameters identified at step 104 is generated at 112. The pulse sequence may then be applied at step 114 as the patient is translated continuously through the imaging volume for data acquisition.

Therefore, in accordance with one embodiment of the present invention, a method of slice selective magnetization preparation for moving table MRI comprises the steps of defining a fixed imaging slab. The process further includes the step of applying a preparation RF pulse to prepare a region of interest outside the fixed imaging slab. The prepared region of interest is then translated to the fixed imaging slab whereupon an imaging RF pulse is applied to the fixed imaging slab to acquire MR data of the prepared region of interest.

In accordance with another embodiment of the invention, an MRI apparatus includes an MRI system having a plurality of gradient coils positioned about a bore of a magnet to impress a polarizing magnetic field and spatially encode spins. An RF transceiver system and an RF switch are controlled by a pulse module to transmit and receive RF signals to and from an RF coil assembly to acquire MR images. The MRI apparatus also includes a computer programmed to receive a user input identifying a preparation interval (e.g. TI) for a pulse sequence to acquire data of a subject being continuously translated through an imaging volume. From the preparation interval, the computer is programmed to determine an offset value, $f_{off}$, to be applied to a preparation RF pulse of the pulse sequence to modify application of the preparation RF pulse to account for translation of the subject through the imaging volume. The computer is also programmed to generate a modified pulse sequence such that application of the preparation RF pulse has been modified by the offset value.

In accordance with another embodiment of the invention, the invention is embodied in a computer program stored on a computer readable storage medium and having instructions which, when executed by a computer, cause the computer to determine a distance spins of a patient will travel while the patient is translated through an imaging volume by a moving table. The computer is also caused to determine, from the distance, a preparation volume of interest. The instructions also cause the computer to generate an imaging sequence to acquire data from a patient being translated past a fixed imaging volume such that the preparation volume of interest is prepared before being presented in the fixed imaging volume.

The present invention has been described in terms of the preferred embodiment, and it is recognized that equivalents, alternatives, and modifications, aside from those expressly stated, are possible and within the scope of the appending claims.

The invention claimed is:

1. A method of slice selective magnetization preparation for moving table MRI, the method comprising the steps of:
    defining a fixed imaging slice within an optimal imaging volume of an MR system;
    determining an offset value from a product of translation distance of a spin at a user-defined TI, amplitude of a slice selective gradient applied to the imaging volume, and a gyromagnetic ratio;
    applying a preparation RF pulse to prepare a region of interest outside the fixed imaging slice but within the optimal imaging volume;

translating the prepared region of interest to the fixed imaging slice; and;

applying an imaging RF pulse to the fixed imaging slice to acquire MR data of the prepared region of interest.

2. The method of claim 1 wherein the region of interest has a same width as that of the fixed imaging slice.

3. The method of claim 1 further comprising the step of applying a preparation RF pulse to a region of interest different from the fixed imaging slice and acquiring MR data from the region of interest present at the fixed imaging slice.

4. The method of claim 1 further comprising the step of offsetting application of the preparation RF pulse as a function of translation direction.

5. The method of claim 4 further comprising the step of offsetting application of the preparation RF pulse opposite to translation direction.

6. The method of claim 1 further comprising the step of continuously translating the subject through the imaging volume.

7. The method of claim 1 wherein the preparation RF pulse includes an inversion recovery pulse.

8. The method of claim 1 further comprising the step of applying the preparation RF pulse such that a time between application of preparation RF pulses is substantially equivalent to an amount of time needed to translate the subject one imaging slice thickness.

9. An MRI apparatus comprising:

a magnetic resonance imaging (MRI) system having a plurality of gradient coils positioned about a bore of a magnet to spatially encode spins and an RF transceiver system and an RF switch controlled by a pulse module to transmit RF signals to an RF coil assembly to acquire MR images; and a computer programmed to:

receive a user input identifying a preparation interval, TI, for a pulse sequence that acquires data of a subject being continuously translated through an imaging volume;

from the preparation interval, determine a frequency offset value, $f_{off}$, to be applied to a preparation RF pulse of the pulse sequence;

modify application of the preparation RF pulse to account for translation of the subject through the imaging volume;

generate a modified pulse sequence such that the preparation RF pulse has been modified by the offset value; and wherein the offset value is defined by:

$$f_{off} = \gamma * A_{ss} * v * TI,$$

where $\gamma$ is a gyromagnetic ratio, $A_{ss}$, is an amplitude of a slice selective gradient applied during the preparation RF pulse, v is a velocity of the subject being translated, and TI is a preparation interval.

10. The MRI apparatus of claim 9 wherein the computer is further programmed to determine a direction of subject translation and apply the offset value to the preparation RF pulse opposite to the direction of subject translation.

11. The MRI apparatus of claim 9 wherein the modified preparation RF pulse includes an inversion recovery pulse.

12. The MRI apparatus of claim 9 wherein the computer is further programmed to repeat application of each preparation RF pulse at a time substantially equivalent to that needed to translate the subject one slice thickness.

13. The MRI apparatus of claim 9 wherein the modified pulse sequence includes a gradient echo sequence.

14. The MRI apparatus of claim 9 wherein the computer is further programmed to change at least one of the preparation interval and the preparation sequence in a prescribed manner as the subject is translated.

15. A computer readable storage medium having a computer program stored thereon to acquire MR data of a patient being translated through an imaging volume, the computer program having a set of instructions that when executed causes a computer to:

determine a distance spins of a magnetization prepared tissue of a patient will travel while the patient is translated through an imaging volume by a moving table during a prescribed preparation interval defined as the time between application of a saturation pulse and commencement of an imaging pulse sequence;

determine, from the distance, a preparation volume of interest;

generate an imaging pulse sequence to acquire MR data from a patient being translated past a fixed imaging volume such that the preparation volume of interest is prepared before being presented in the fixed imaging volume; and wherein the set of instructions further causes the computer to determine an amplitude of a slice selective gradient and multiply the amplitude and a gyromagnetic ratio to the distance to determine the frequency offset of the preparation pulse.

16. The computer readable storage medium of claim 15 wherein the computer is further programmed to identify the preparation volume of interest relative to the fixed imaging volume in a direction opposite of table translation.

17. The computer readable storage medium of claim 16 wherein the computer is further programmed to define the preparation volume of interest to have the same slice thickness as the fixed imaging volume.

18. The computer readable storage medium of claim 15 wherein each preparation RF pulse has a flip angle of 180°.

19. The computer readable storage medium of claim 15 wherein imaging volume includes one of a single slice and a slab of multiple slices.

* * * * *